United States Patent
Slater et al.

(10) Patent No.: US 6,796,936 B2
(45) Date of Patent: *Sep. 28, 2004

(54) IMPLANTABLE RADIATION THERAPY DEVICE HAVING CONTROLLABLE RADIATION EMISSION

(75) Inventors: Charles R. Slater, Fort Lauderdale, FL (US); Scott L. Jahrmarkt, Miami Beach, FL (US); Scott T. Smith, Miami, FL (US); Kevin W. Smith, Coral Gables, FL (US)

(73) Assignee: Syntheon, LLC, Miami, FL (US)

(*) Notice: Subject to any disclaimer, the term of this patent is extended or adjusted under 35 U.S.C. 154(b) by 0 days.

This patent is subject to a terminal disclaimer.

(21) Appl. No.: 10/281,777

(22) Filed: Oct. 28, 2002

(65) Prior Publication Data

US 2003/0088146 A1 May 8, 2003

Related U.S. Application Data

(63) Continuation of application No. 09/575,431, filed on May 22, 2000, now Pat. No. 6,471,631, which is a continuation-in-part of application No. 09/200,698, filed on Nov. 27, 1998, now Pat. No. 6,066,083.

(51) Int. Cl.[7] .......................... A61M 36/12; A61N 5/00
(52) U.S. Cl. ............................................................ 600/8
(58) Field of Search .................................... 600/1–8

(56) References Cited

U.S. PATENT DOCUMENTS

| | | | |
|---|---|---|---|
| 1,954,868 A | 4/1934 | Failla et al. | 174/177 |
| 3,351,049 A | 11/1967 | Lawrence | 128/1.2 |
| 4,323,055 A | 4/1982 | Kubiatowicz | 128/1.2 |
| 4,702,228 A | 10/1987 | Russell, Jr. et al. | 128/1.2 |
| 4,784,116 A | 11/1988 | Russell, Jr. et al. | 128/1.2 |
| 4,815,449 A | 3/1989 | Horowitz | 600/7 |
| 4,891,165 A | 1/1990 | Suthanthiran | 252/633 |
| 4,994,013 A | 2/1991 | Suthanthiran | 600/88 |
| 5,011,677 A | 4/1991 | Day et al. | 424/1.1 |
| 5,012,357 A | 4/1991 | Schoeppel et al. | 378/65 |
| 5,163,896 A | 11/1992 | Suthanthiran et al. | 600/8 |
| 5,176,617 A | 1/1993 | Fischell et al. | 600/3 |
| 5,213,561 A | 5/1993 | Weinstein et al. | 600/3 |
| 5,302,168 A | 4/1994 | Hess | 600/3 |
| 5,342,283 A | 8/1994 | Good | 600/8 |
| 5,405,309 A | 4/1995 | Carden, Jr. | 600/3 |
| 5,503,614 A | 4/1996 | Liprie | 600/7 |
| 5,713,828 A | 2/1998 | Coniglione | 600/7 |
| 5,728,042 A | 3/1998 | Schwager | 600/3 |
| 5,863,284 A | 1/1999 | Klein | 600/3 |
| 5,924,974 A | 7/1999 | Loffler | 600/3 |
| 6,007,475 A | 12/1999 | Slater et al. | 600/8 |
| 6,066,083 A | 5/2000 | Slater et al. | 600/8 |
| 6,080,099 A | 6/2000 | Slater et al. | 600/8 |
| 6,183,410 B1 | 2/2001 | Jacobsen et al. | 600/3 |
| 6,210,316 B1 | 4/2001 | Slater et al. | 600/8 |
| 6,238,332 B1 | 5/2001 | Kanesaka | 600/3 |
| 6,471,631 B1 | 10/2002 | Slater et al. | 600/8 |

*Primary Examiner*—John P. Lacyk
(74) *Attorney, Agent, or Firm*—Gordon & Jacobson, PLLC (57) ABSTRACT

An implantable radiation therapy device includes a biocompatible radiotranslucent outer capsule containing a radiation shielding element and a radioactive isotope at least partially shielded by the shielding element. When the device is at or below body temperature, radiation is prevented or limited from being transmitted through the outer capsule by the shielding element. When non-ambient energy is applied to the device, the shielding element and radioactive isotope are reconfigured such that an increased level of radiation is transmitted through the outer capsule and emitted by the device.

13 Claims, 8 Drawing Sheets

IMPLANTABLE RADIATION THERAPY DEVICE HAVING CONTROLLABLE RADIATION EMISSION

This is a continuation of application Ser. No. 09/575,431, filed May 22, 2000 now U.S. Pat. No. 6,471,631 which in turn is a continuation-in-part of Ser. No. 09/200,698, filed Nov. 27, 1998 now U.S. Pat. No. 6,066,083 is hereby incorporated by referenced herein in its entirety.

BACKGROUND OF THE INVENTION

1. Field of the Invention

The invention relates to implantable radiation therapy devices. More particularly, the invention relates to improved radiation therapy and brachytherapy devices, also known as radioactive therapeutic seeds, for the treatment of oncological and other medical conditions.

2. State of the Art

Radioactive seed therapy is a well known and well accepted medical procedure for the treatment of various oncological and other medical conditions. Seed therapy, also known as interstitial brachytherapy typically involves the implantation of one to one hundred relatively small capsules (seeds) into or around a treatment site. The capsules contain a radioactive isotope which irradiates the treatment site at close range without adversely affecting other parts of the body. Brachytherapy has been used successfully in the treatment of various types of cancers such as prostate cancer. It has also been used to prevent the growth or regrowth of tissues in the treatment of various occlusive diseases such as arteriosclerosis and arthrosclerosis subsequent to balloon angioplasty.

Radioactive therapeutic seeds are carefully designed to possess several important qualities. First, in the case of prostatic interstitial brachytherapy they should be relatively small, approximately 0.025 inch in diameter and approximately 0.16 inch long so that they may be implanted into the prostate gland using minimally invasive instruments and techniques. However, it should be appreciated by those skilled in the art that implantable radioactive sources come in all shapes and sizes. Second, the radioactive isotope must be enclosed in a biocompatible protective package since the seeds are typically not removed and will remain in the body for many years. Third, each seed preferably includes a radiopaque (e.g. high Z material) marker so that it can be located at the treatment site with the aid of fluoroscopy.

The state of the art of radioactive therapeutic seeds is substantially disclosed in seven U.S. Pat. No. 5,713,828 to Coniglione for "Hollow-Tube Brachytherapy Device", U.S. Pat. No. 5,405,309 to Carden, Jr. for "X-Ray Emitting Interstitial Implants", U.S. Pat. No. 4,891,165 to Suthanthiran for "Device and Method for Encapsulating Radioactive Materials" and U.S. Pat. No. 4,784,116 to Russell, Jr. et al. for "Capsule for Interstitial Implants", U.S. Pat. No. 4,702,228 to Russell, Jr. et al. for "X-Ray Emitting Interstitial Implants", U.S. Pat. No. 4,323,055 to Kubiatowicz for "Radioactive Iodine Seed", and U.S. Pat. No. 3,351,049 to Lawrence for "Therapeutic Metal Seed Containing within a Radioactive Isotope Disposed on a Carrier and Method of Manufacture", which are each incorporated by reference herein in their entireties. In addition, the art has been significantly advanced in co-owned U.S. Ser. Nos. 09/133,072, 09/133,081, and 09/133,082, which are hereby incorporated by reference herein in their entireties.

The Lawrence patent, which issued in 1967, describes many of the essential features of radioactive therapeutic seeds. Lawrence describes radioactive isotopes (I-125, Pd-103, Cs-131, Xe-133, and Yt-169) which emit low energy X-rays and which have relatively short half-lives. When implanted at a treatment site, these isotopes provide sufficient radiotherapy without posing a radiation danger to the medical practitioner(s), people in the vicinity of the patient, or other parts of the patient's body. Lawrence further describes a protective capsule which contains the isotope and prevents it from migrating throughout the body where it might interfere with healthy tissue. The capsule is cylindrical and made of low atomic number biocompatible materials such as stainless steel or titanium which do not absorb X-rays. The isotope is coated on a rod shaped carrier made of similar X-ray transparent (e.g. low Z) material and is placed inside the capsule cylinder which is then closed. The other patents each provide some improvement over the original Lawrence design.

Despite the fact that radioactive therapeutic seeds have been in use for over thirty years and despite the several significant improvements made in the seeds, many concerns still exist regarding the use of the seeds. One problem is that prior to and during implantation of the therapeutic seeds, the physician must handle the radioactive seeds, and therefore take precautions to limit his or her exposure. The precautions may include the use of lead lined clothing and limiting the time for completing any one procedure. However, such clothing is generally heavy and tiring to wear, and limiting procedure time may not be in the best interest of the patient.

In addition, it is difficult to store radioactive therapeutic seeds, as special radiation shielding materials must be used in the container storing the seeds.

Moreover, there may be situations in which it is desirable to increase the level of radiation emitted by a seed after implantation, or keep the level of radiation at a certain level, despite the natural decay of the radioactive source over a more prolonged period of time. For example, it may be desirable to provide a first dosage of radiation for a period of time and then, based upon a later diagnosis, increase the dosage for a second period of time. With the present radioactive implants of the art this can only be done through a subsequent invasive procedure of implanting additional seeds, as radioactive elements decrease their radiation output according to their respective half-life.

None of the art addresses any manner of providing an "inactive" seed which can later, e.g., after implantation, be activated to emit radiation. Likewise, none of the art addresses otherwise increasing the amount of radiation emitted by the seed after the seed is implanted in the patient, or maintaining a level of radiation over a longer period of time than the half-life of the radioactive isotope in the implant would otherwise permit.

SUMMARY OF THE INVENTION

It is therefore an object of the invention to provide radioactive therapeutic seeds which have means for controllably altering the radiation transmitted through the seed capsule.

It is also an object of the invention to provide radioactive therapeutic seeds which are controllably activated to "turn on" the seeds to cause radiation to be emitted therefrom or to increase the radiation emitted therefrom.

In accord with these objects which will be discussed in detail below, the radioactive brachytherapy seeds of the present invention generally include an outer capsule containing a radioactive material, and a substantially radiopaque shield which in a first (pre-implantation) configuration substantially obstructs radiation emitted by the radioactive material. One or both of the radioactive material and the shield are controllably movable relative to the other into a second (post-implantation) configuration such that the radioactive material is at least partially unobstructed by the shield. As a result, the level of radiation emitted by the seed is increased. For purposes herein, "radiopaque" refers to the property of having a relatively "high Z" value, and the terms "radiopaque" and "high Z" are used interchangeably herein.

Various embodiments of the radioactive material and the radiopaque shield are provided. In a first embodiment, a low melt temperature low Z material, e.g., wax, includes radioactive particles suspended therein. The low Z material is preferably substantially provided entirely within a high Z casing. The low Z material, with radioactive particles therein, may be heated and forced to flow, by pressurized fluid or mechanical means, through an opening in the high Z casing to at least partially surround the high Z casing and substantially cause the seed to emit radiation. In a second embodiment, an elastic or heat shrinkable casing is stretched over a radioactive material and a high Z material is deposited on the casing. When the radioactive material is heated to a melted state, the force of the casing on the radioactive material moves the radioactive material out of the casing, the casing collapses, and the radioactive material surrounds the high Z material on the casing to initiate or increase radiation emission from the seed. In a third embodiment, a flowable radioactive material is retained within a radiopaque casing by a removable barrier. The barrier may be removed by melting (e.g., a wax stopper barrier), breaking, or by a valve mechanism, and a pressurizing agent then forces the flowable radioactive material to surround the radiopaque casing. In a fourth embodiment, a first member is provided with regions upon which a radioactive isotope is deposited. The first member is disposed within a second member which includes one or more substantially radiopaque regions through which transmission of radiation is limited and one more substantially radiotransparent regions through which the radiation may be transmitted. In a first configuration, the radiopaque regions are positioned over the radioactive isotope regions. The first member may be controlled to move relative to the second member, e.g., by heat, vibration, or inertia, into a second configuration wherein the radiotransparent regions are positioned over the isotope and substantially permit the emission of radiation by the seed. In a fifth embodiment, a radiopaque shape memory alloy coil element is provided over an elongate element having an isotope deposited on a portion thereof. The rings of the coil are in a naturally compressed state over the portion of the elongate element on which an isotope is provided to prevent transmission of radiation through the rings of the coil and out of the outer capsule. The coil is trained to expand when heated and expose the portion of the elongate element provided with the isotope. In a sixth embodiment, a plurality of radiopaque shape memory alloy elements are provided, with each element having a portion on which an isotope is deposited. The portions provided with the isotope are initially oriented inward such that they do not emit radiation through the outer capsule. The elements are trained such that when they are heated, the elements change shape (or otherwise move) to substantially expose the portions provided with the isotope and thereby substantially initiate emission of radiation.

It will be appreciated that in embodiments utilizing heat to "activate" the seed, the heat may be provided by hot water, microwave technology, or other radiating means provided at or near (e.g., from adjacent to a few feet away) the seed implant site. Additional means for substantially "activating" or at least increasing seed radioactivity may also be used.

It will be further appreciated that the ability to control the amount of radiation emitted by the seed enables the physician to "turn on" the seed or at least increase the radiation emitted by the seed when desired; i.e., upon the application of non-ambient energy, preferably of a predetermined amount. In addition, the seeds may be relatively safely handled without cumbersome precautions prior to activation.

Additional objects and advantages of the invention will become apparent to those skilled in the art upon reference to the detailed description taken in conjunction with the provided figures.

DETAILED DESCRIPTION OF THE PREFERRED EMBODIMENTS

Figure 1:
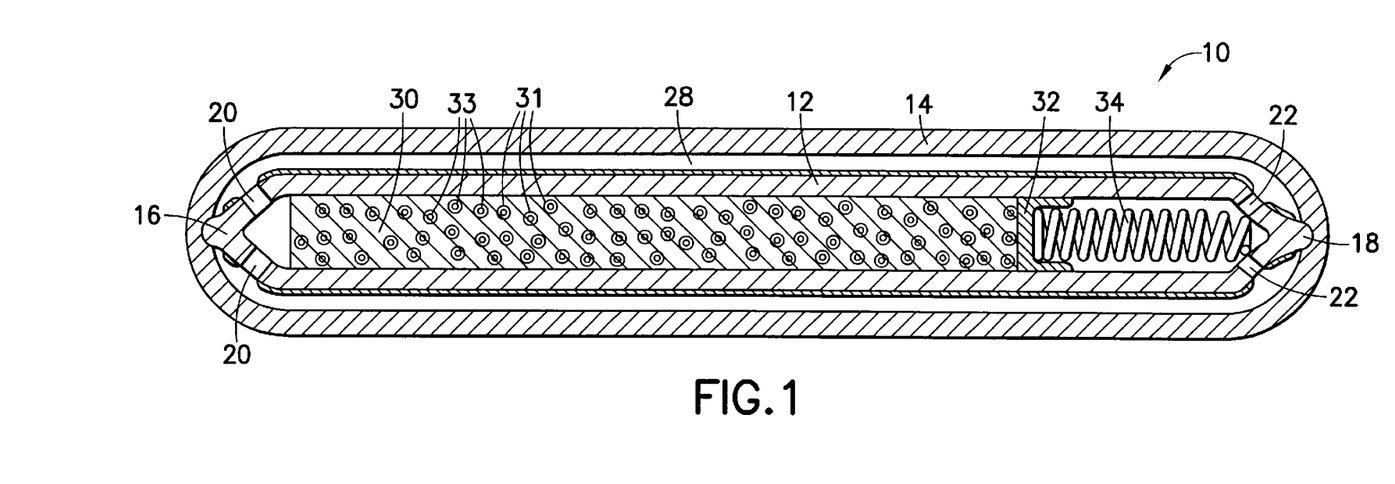
FIG. 1 is a section view of a first embodiment of an at least partially activatable brachytherapy seed in an "inactive" configuration.
Figure 1A:
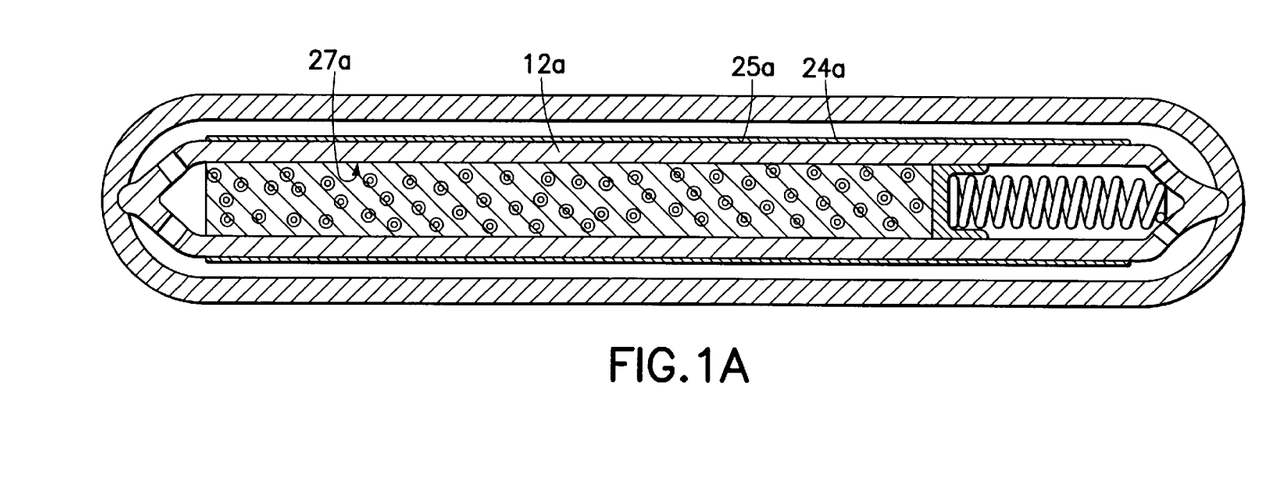
FIG. 1A is a section view of an alternate first embodiment of an at least partially activatable brachytherapy seed in an "inactive" configuration.

Referring now to FIG. 1, a radiation therapy seed 10 according to the invention is shown. The seed 10 includes an inner capsule 12, preferably made from a radiopaque material, such as lead, provided within a biocompatible outer capsule 14, preferably made from titanium, aluminum, stainless steel, or another substantially radiotranslucent material. Alternatively, referring to FIG. 1A, the inner capsule may be made from a radiotranslucent material and its exterior surface 25a may be coated or other provided with, e.g., as a sleeve, a radiopaque material 24a. Furthermore, while not preferred, the radiopaque material may be provided to the interior surface 27a of the inner capsule 12a (either by deposition thereon or an internal sleeve provided thereagainst). The outer capsule 14 is sealed closed about the inner capsule 12 according to any method known in the art, including the methods disclosed in previously incorporated U.S. Ser. No. 09/133,081. For treatment of the prostate, the outer capsule preferably has a diameter of less than 0.10 inches, and more typically a diameter of less than 0.050 inches, and preferably has a length of less than 0.50 inches, and more typically a length of less than 0.16 inches.

The inner capsule 12 includes first and second ends 16, 18, and respective first and second openings 20, 22 at the respective ends. The inner capsule 12 is preferably coaxially held within the outer capsule 14 at the first and second ends 16, 18 of the inner capsule 12, such that a preferably uniform space 28 is provided between the inner and outer capsules.

At the first end 16, the inner capsule 12 is at least partially filled with a meltable solid radioactive material 30. The radioactive material is preferably a low temperature melting, low Z carrier in which particles 31 provided with a radioactive isotope 33 are suspended. For the carrier, a low melting point is preferably characterized by under 160° F., and more preferably under 140° F. but over 105° F., such that at room temperature and body temperature, the seed is inactive as the radioactive material is substantially contained within the radiopaque inner capsule 12. Wax is a preferred carrier, although other carriers such as certain metals and polymers may be used. Exemplar isotopes include I-125, Pd-103, Cs-131, Xe-133, and Yt-169, which emit low energy X-rays and which a have relatively short half-life.

A piston 32 is provided in the inner capsule 12 and, upon the liquefaction of the radiopaque material 30, is capable of moving, e.g., by sliding, along a length of the inner capsule. A spring element 34 is provided between the second end 18 of the inner capsule 12 and the piston 32, forcing the piston against the radiopaque material.

Figure 2:
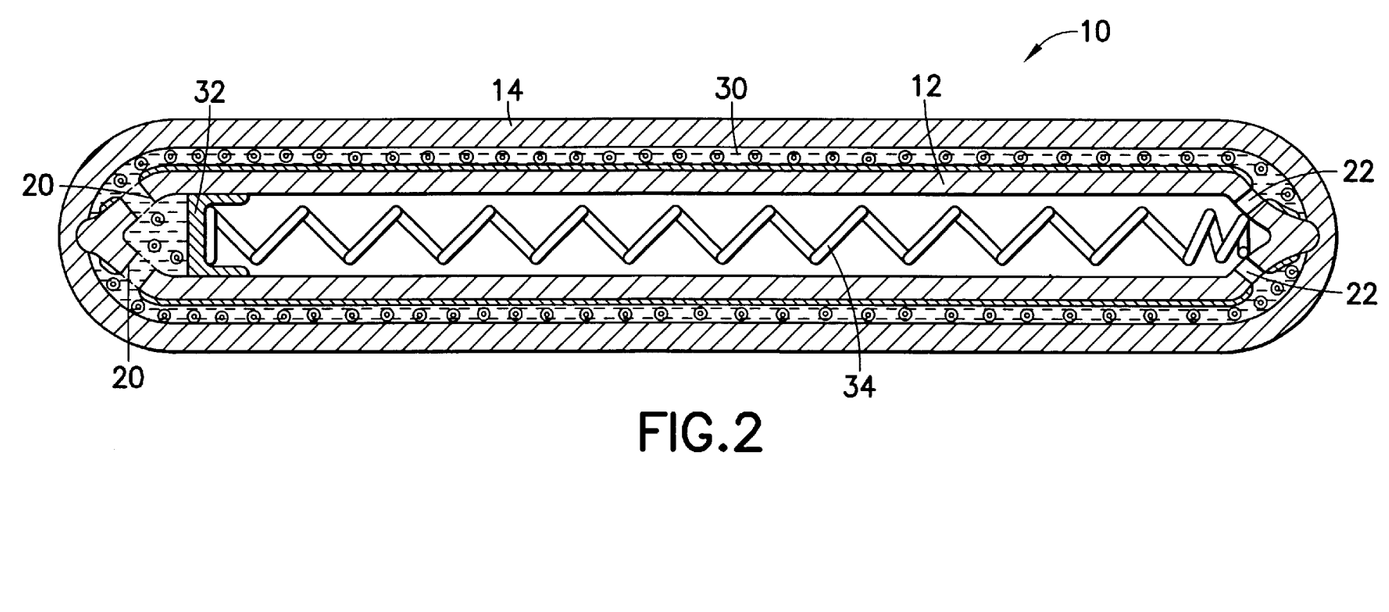
FIG. 2 is a section view of the first embodiment of an at least partially activatable brachytherapy seed in an "activated" configuration.

Turning now to FIG. 2, when it is desired to increase or initiate radiation emission by the seed, that is, "activate" the seed, the seed may be "activated" by applying heat which causes the radioactive material 30 to melt. The heat may be applied, for example, by hot water provided in the urethra (for seeds implanted to treat prostatic conditions), by microwave radiation, or by other types of radiation. The spring element 34 provides force against the piston 32 which, in turn, forces the radioactive material 30 out of the first openings 20 and into the space 28 between the inner and outer capsules 12, 14. The second openings 22 permit gas trapped between the inner and outer capsules 12, 14 to be moved into the inner capsule 12 as the radioactive material 30 flows and surrounds the radiopaque inner capsule 12. It will also be appreciated that second openings 22 are not required if the space 28 is evacuated during manufacture. Once the radioactive material has surrounded the inner capsule, the capsule is substantially "activated".

In a variation of the above, it will be appreciated that some radioactive particles 31 or the isotope 33 may be initially provided outside the inner capsule (on the exterior surface of inner capsule, interior surface of outer capsule, or within space 28), such that movement of the radioactive material 30 out of the inner capsule operates to increase, rather than activate, radiation emission by the seed 10.

Figure 3:
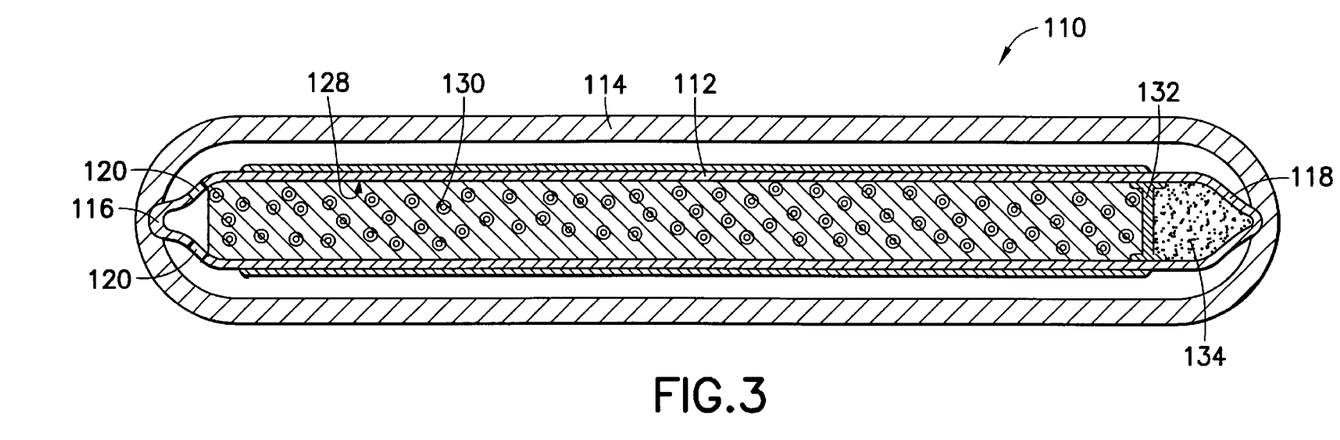
FIGS. 3 and 4 are section views of a second embodiment of an at least partially activatable brachytherapy seed in "inactive" and "active" seed configurations, respectively.

Referring now to FIG. 3, according to a second embodiment of the invention, substantially similar to the first embodiment, the radiation therapy seed 110 includes a radiopaque inner capsule (or inner cylinder) 112 provided within a radiotransparent outer capsule 114. The inner capsule 112 includes first and second ends 116, 118, and one or more openings 120 at the first end. A solid, low temperature melting, radioactive material 130 is provided within the inner capsule 112.

A piston 132 is provided in the inner capsule 112 against the radioactive material 130, and a pressurized fluid (liquid or gas) 134 is provided between the piston 132 and the second end 118 of the inner capsule urging the piston toward the first end 116.

Figure 4:
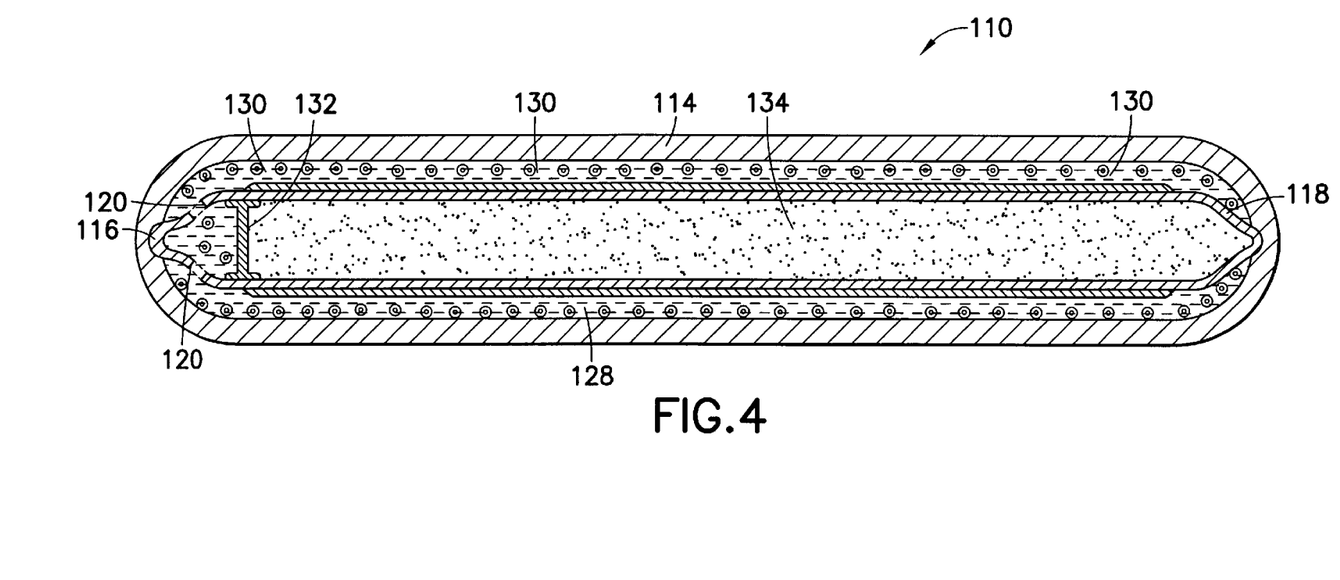

Turning now to FIG. 4, the seed 110 may be "activated" by applying heat energy which causes the radioactive material 130 to melt. The pressurized fluid 134 then moves the piston 132 away from the second end 118, and the piston 132 moves the melted radioactive material 130 through the first openings 120 in the inner capsule into the space 128 between the inner capsule 112 and the outer capsule 114. Flow of the radioactive material 130 such that the radioactive material surrounds the inner capsule 112 is thereby facilitated.

Figure 5:
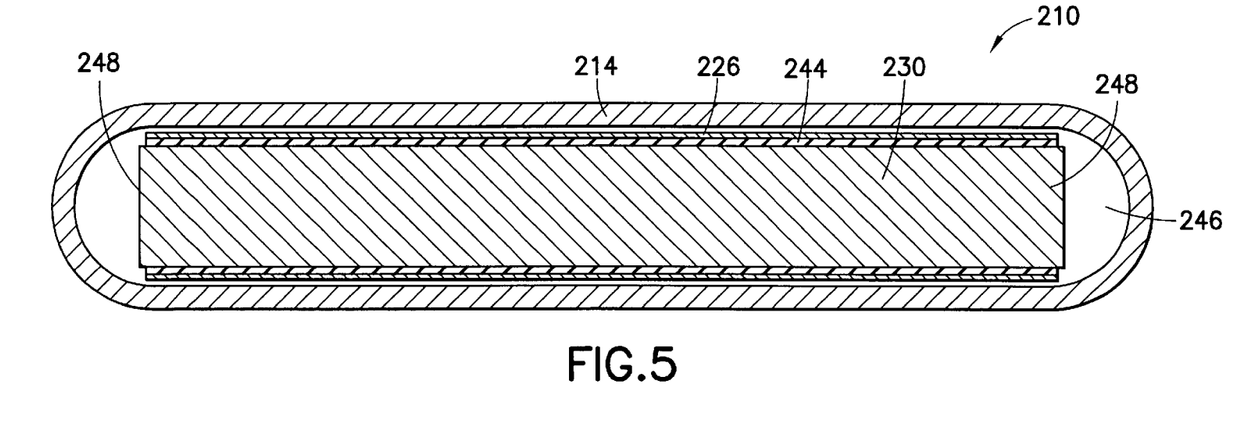
FIGS. 5 and 6 are section views of a third embodiment of an at least partially activatable brachytherapy seed in "inactive" and "active" seed configurations, respectively.

Referring now to FIG. 5, according to a third embodiment of the invention, the radiation therapy seed 210 includes a capsule 214 having therein a rod 230 formed from a low melting point radioactive material which is provided with an elastic cover 244, e.g., latex, stretched thereover. Alternatively, the cover may be made from a heat shrinkable material. The cover 244 is provided with a radiopaque coating 226 thereon. The rod 230 and cover 244 preferably substantially fill the interior 246 of the capsule 214. As such, radiation emission is limited to the ends 248 of the rod.

Figure 6:
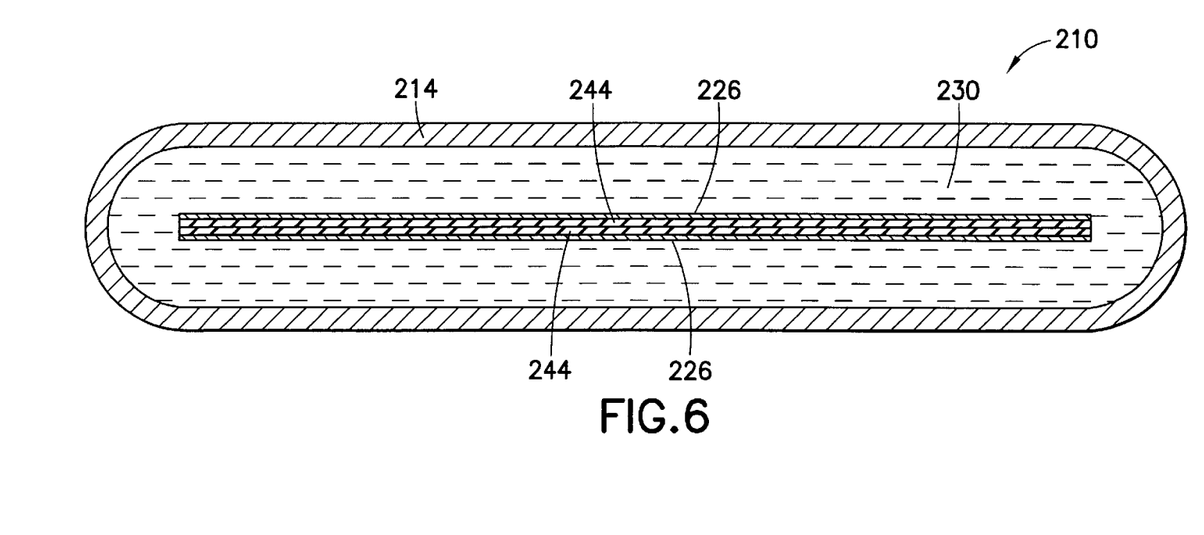

Turning now to FIG. 6, when the capsule 214 is heated, the rod 230 liquefies and the cover 244 collapses inward to force the radioactive material out from within the cover. The radioactive material 230 thereby surrounds the collapsed cover 244, with radiopaque material 226 deposited thereon, and increases the radioactive emission by the seed 210.

Figure 7:
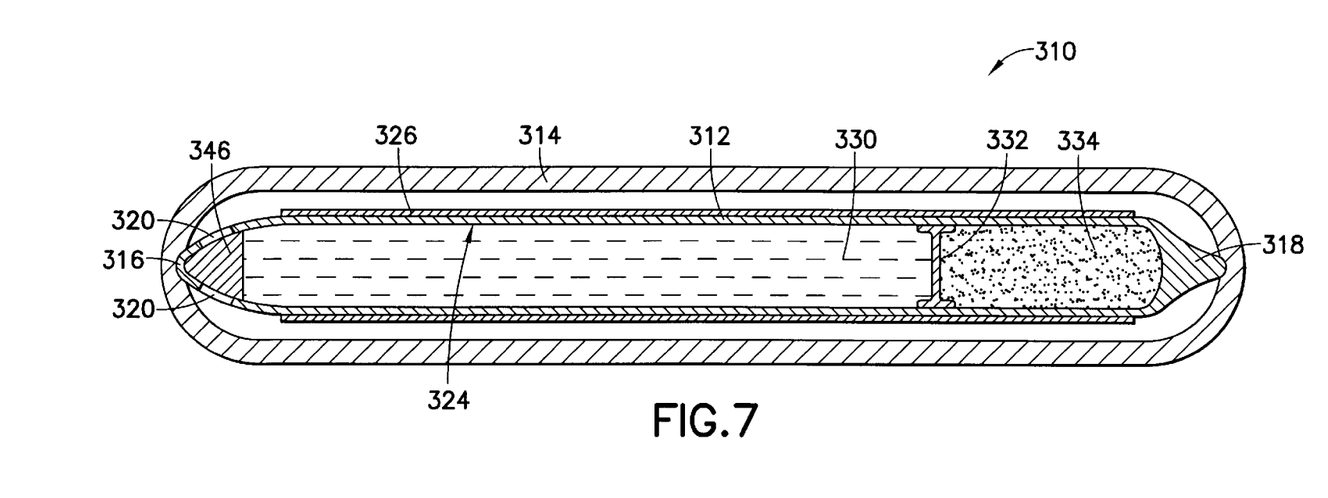
FIGS. 7 and 8 are section views of a fourth embodiment of an at least partially activatable brachytherapy seed in "inactive" and "active" seed configurations, respectively.

Referring now to FIG. 7, according to a fourth embodiment of the invention, the radiation therapy seed 310 includes an inner capsule 312 provided within an outer capsule 314. The inner capsule 312 includes first and second ends 316, 318. The first end 316 includes openings 320. A high Z material 326 is deposited on a surface 324 of the inner capsule 312. Alternatively, the inner capsule is made from a high z material. The inner capsule is preferably coaxially held within the outer capsule, and preferably a vacuum is provided therebetween.

The inner capsule 312 is partially filled with a radioactive material 330 which is liquid at body temperature, e.g., a dissolved radioactive compound. The inner capsule is also provided with a pressurized fluid (gas or liquid) 334. A piston 332 separates the radioactive material 330 and the pressurized fluid 334. The liquid material 330 is contained within the inner capsule by a wax plug 346 or the like, which is substantially solid at body temperature and which blocks the passage of the liquid radioactive material 330 through the openings 320 at the first end 316 of the inner capsule 312.

Figure 8:
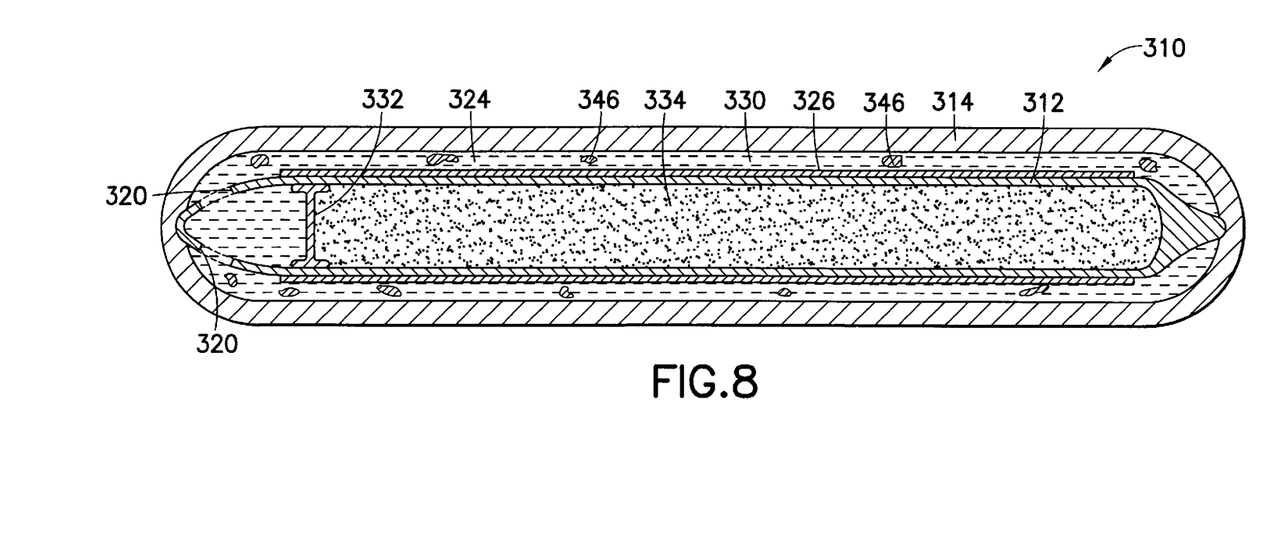

Turning now to FIG. 8, when the seed 310 is heated, the plug 346 is melted and the pressurized fluid 334 forces the melted plug 346 and radioactive material 330 to exit the openings 320 at the first end 316 of the inner capsule 312 and surround the inner capsule and high Z material 326 thereof such that radiation may be emitted by the seed.

It will be appreciated that as an alternative to a wax plug 346 or the like, a frangible disc or valve may be utilized to retain the liquid radioactive material. The disc or valve may be operated via heat or mechanical means to controllably permit the radioactive material to flow out of the inner capsule.

Figure 9:
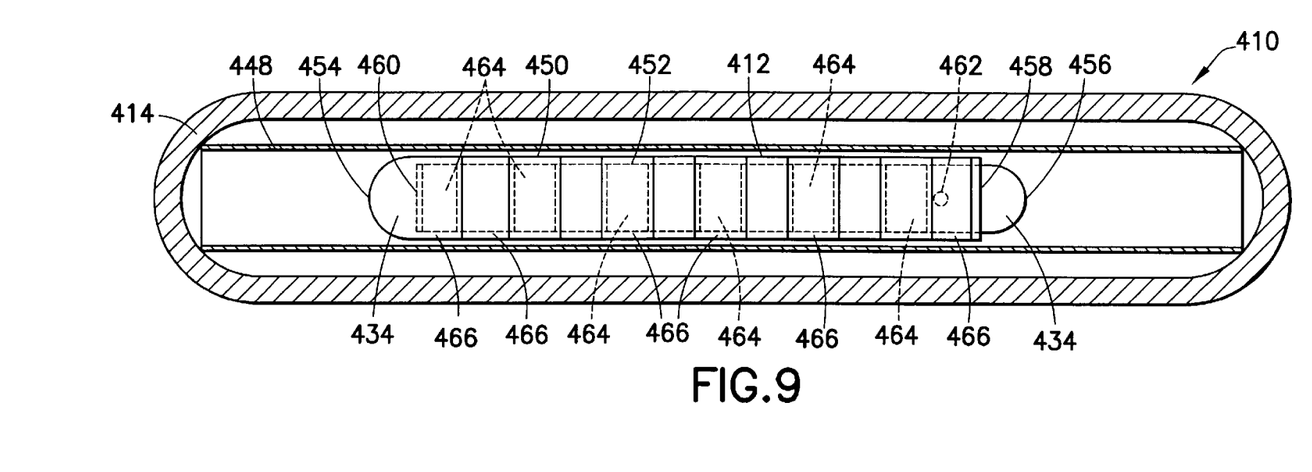
FIGS. 9 and 10 are section views of a fifth embodiment of an at least partially activatable brachytherapy seed in "inactive" and "active" seed configurations, respectively.

Referring now to FIG. 9, according to a fifth embodiment of the invention, the radiation therapy seed 410 includes an inner capsule 412 provided within an outer capsule 414. The inner capsule 412 is preferably held substantially coaxial within the outer capsule by a gas permeable tube 448, e.g., a mesh or perforate tube formed of a low Z metal or plastic. The inner capsule 412 is comprised of first and second preferably substantially tubular components 450, 452, each having a closed end 454, 456, respectively, and an open end 458, 460, respectively. The open end 458 of the first component 450 is sized to receive therein at least the open end 460 and a portion of the second component 452. The first and second components 450, 452 together thereby form a "closed" inner capsule 412. At least one of the first and second components is provided with a hole 462 which is blocked by the other of the first and second components when the inner capsule is in the "closed" configuration. A gas 434 is provided in the closed inner capsule 412.

The first component and second components 450, 452 are made from a substantially low Z material. The second component 452 is provided with a plurality of preferably circumferential bands 464 of a radioactive material, while the first component 450 is provided with a plurality of preferably circumferential bands 466 of a high Z material. The first and second components are fit and aligned together such that along the length of the inner capsule 412 a series of bands in which the radioactive material 464 is covered by the high Z material 466 are provided. The bands 466 of high Z material substantially block the transmission of radiation at the isotope bands 464.

Figure 10:
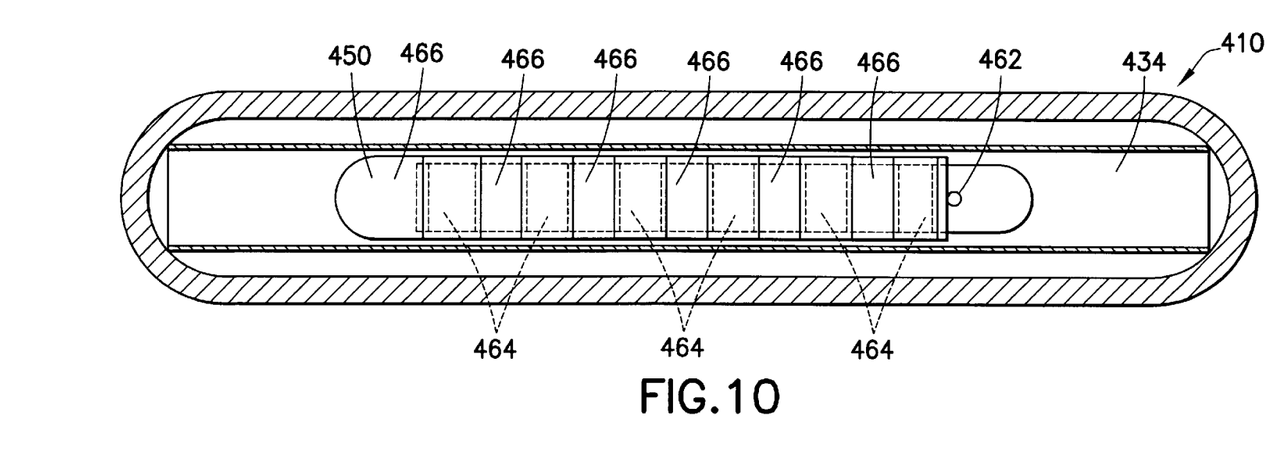

Turning now to FIG. 10, when the seed 410 is heated, the gas 434 within the inner capsule 412 increases in pressure and forces the second component axially away from the first component such that the volume of the inner capsule increases. As the first and second components 450, 452 move axially apart, the hole 462 becomes exposed which equalizes the pressure between the interior of the inner capsule 412 and the interior of the outer capsule 414, terminating the axial movement. The hole 462 is preferably positioned such that movement is terminated with the high Z bands 466 of the first component 450 substantially alternating with the radioactive isotope bands 464 of the second component 452, such that the seed is activated for radiation emission.

It will be appreciated that the other means may be used to move the first and second components 450, 452 relative to each other. For example, a one-way inertial system or an electromagnetic system may be used. In addition, it will be appreciated that the inner capsule 412 may be configured such that the high Z bands 466 initially only partially block the radioactive isotope bands 464; i.e., that the seed 410 may be activated from a first partially activate state to a second state with increased radioactive emission.

Figure 11:
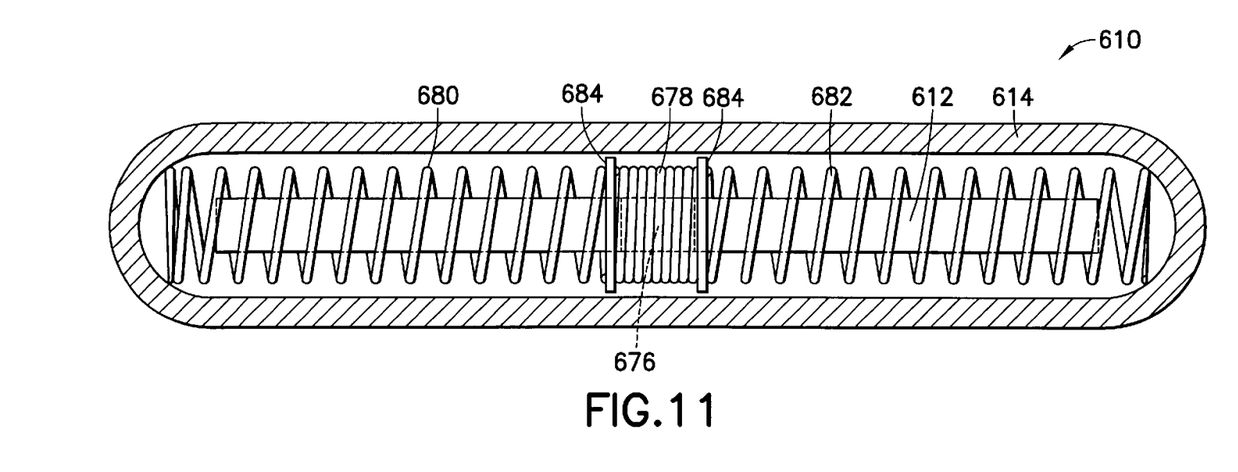
FIGS. 11 and 12 are section views of a sixth embodiment of an at least partially activatable brachytherapy seed in "inactive" and "active" seed configurations, respectively.

Referring now to FIG. 11, according to a sixth embodiment of the invention, a radiation therapy seed 610 includes an inner wire 612 provided with a circumferential band 676 of radioactive isotope material. A close wound shape memory spring coil 678 is positioned centrally over the inner wire 612 over the band 676 of radioactive material. The shape memory coil 678 is preferably made from a relatively high Z material, e.g., Nitinol, and is trained to expand when subject to a predetermined amount of heat. Second and third spring coils 680, 682 are positioned on either side of the shape memory coil 678 to maintain the high Z coil 687 at the desired location. Washers 684 may be positioned between each of the coils 678, 680, 682 to maintain the separation of the coils; i.e., to prevent the coils from entangling and to better axially direct their spring forces. The wire 612 and coils 678, 680, 682 are provided in an outer capsule 614.

Figure 12:
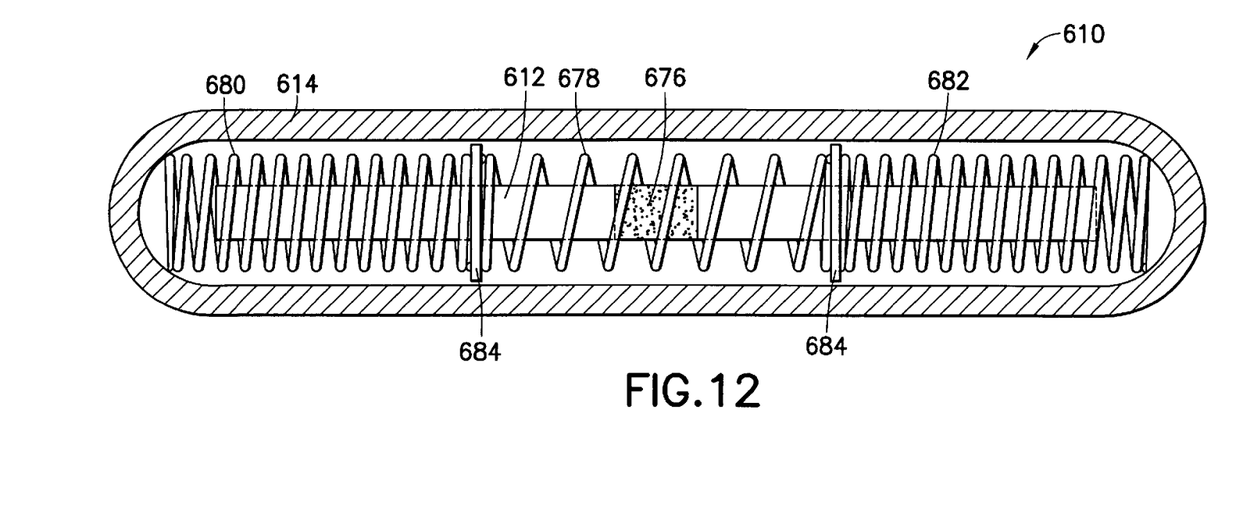

Turning now to FIG. 12, when the seed 610 is subject to a predetermined amount of heat, the shape memory coil 678 expands to substantially expose the isotope band 676 and to thereby activate the seed.

Figure 13:
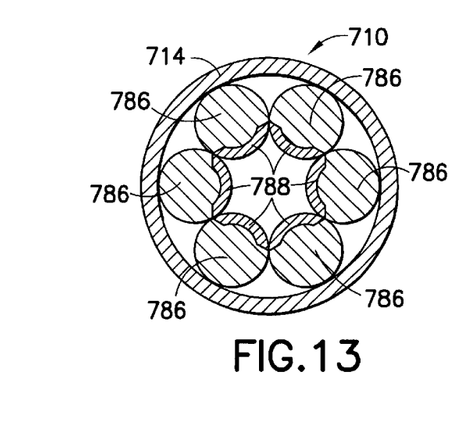
FIGS. 13 through 15 are cross section views of the seventh embodiment of "inactive", "transitional" and "activated" seed configurations, respectively.

Referring now to FIG. 13, according to a seventh embodiment of the invention, a radiation therapy seed 710 includes a relatively radiotranslucent capsule 714 provided with preferably six rods 786 oriented longitudinally in the capsule 714. The rods 786 are made from a shape memory material which preferably is substantially radiopaque, e.g., a nickel titanium alloy. Each end of each rod is provided with a twisted portion 787. In addition, the ends of the rods are secured, e.g., by glue 789 or weld, in the outer capsule 714. When the rods are subject to heat energy, the rods are adapted to untwist at their respective twisted portions 787 about their respective axes. The rods 786 are each provided with a longitudinal stripe 788 (preferably extending about 60° to 120° about the circumference of the rods) of a radioactive isotope along a portion of their length, and preferably oriented in the capsule 714 such that the stripe 788 of each is directed radially inward toward the center C of the capsule with the high Z material of the rod substantially preventing or limiting transmission of radiation therethrough.

Figure 14:
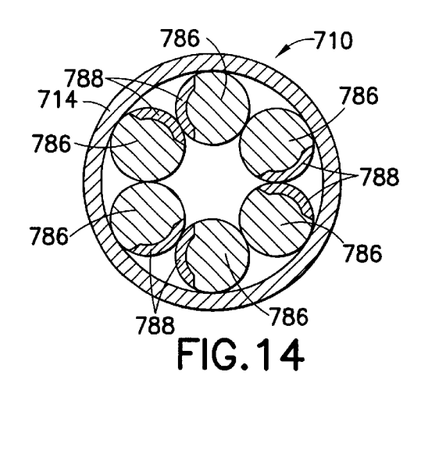
Figure 15:
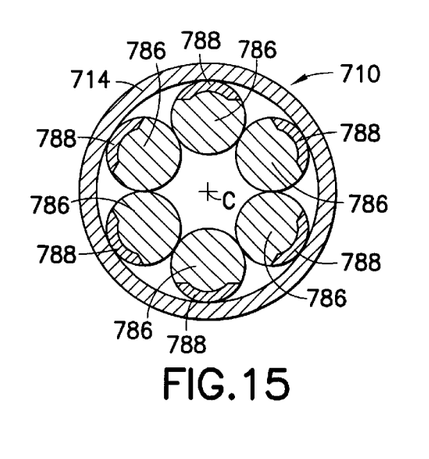

Turning now to FIG. 14, when subject to heat energy, the shape memory rods 786 within the seed 710 twist (or rotate) along their axes. The rods 786 are preferably oriented such that adjacent rods rotate in opposite directions. Turning now to FIG. 15, the rods 786 are trained to rotate preferably 180° about their respective axes. As a result, the isotope stripe 788 along each of the rods 786 is eventually directed radially outward to activate radiation emission by the seed.

It will be appreciated that the rods 786 are not required to be substantially radiopaque and that alternatively, or additionally, the rods may be circumferentially deposited with a relatively high Z material along their length at least diametrically opposite the longitudinal stripes of radioactive isotopes, and preferably at all locations on the rods other than on the stripes 788. Furthermore, it will be appreciated that fewer than six or more than six rods may be provided in the capsule. Moreover, a central rod may also be used to maintain the rods in the desired spaced apart configuration; i.e., such that the rods together form a generally circular cross section.

Figure 16:
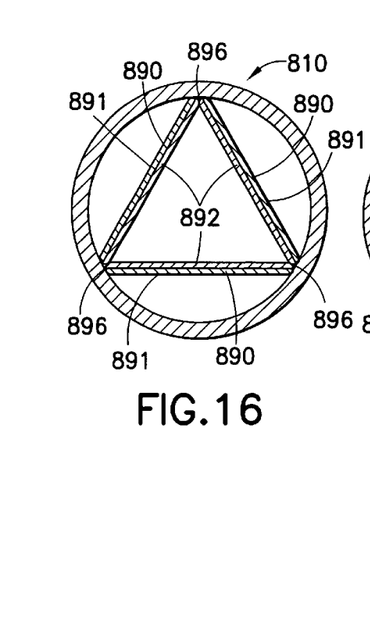
FIGS. 16 through 19 are cross section views of an eighth embodiment of an at least partially activatable brachytherapy seed in "substantially inactive", "first transitional", "second transitional", and "activated" seed configurations, respectively.

Referring now to FIG. 16, according to an eighth embodiment of the invention, a radiation therapy seed 810 includes a relatively radiotranslucent capsule 814 provided with preferably three elongate shape memory strips 890 positioned lengthwise in the capsule 814. It will be appreciated that two or four or more strips 890 may also be used. The strips are preferably made from Nitinol and are also preferably coated with a high z material 891, e.g., gold or a heavy metal, on one side (an initially outer side), and with a radioactive isotope 892 on the side opposite the high Z material (an initially inner side). The strips 890 are preferably positioned in the capsule at 120° relative separation. The configuration of the strips 890 and the high Z material on the outer side of the strips substantially limits radiation emission by the seed, as radiation is emitted only from between the ends of the strips, at 896.

Figure 17:
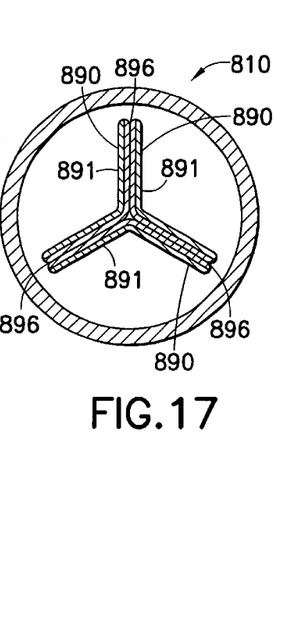
Figure 18:
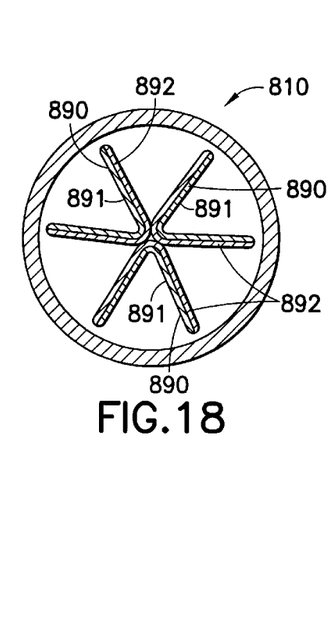
Figure 19:
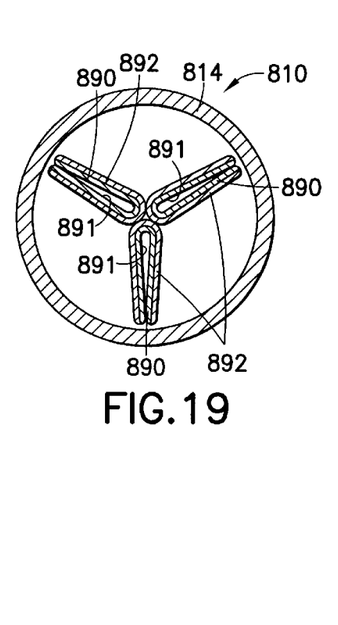

The shape memory strips 890 are trained to bend. As shown in FIGS. 17 through 19, when heat is applied to the seed, the strips 890 fold into their bent configuration such that eventually the radioactive material 892 of the strips 890 is located substantially on an exterior surface of the strips, while the high Z material is located on an interior side of the strips to further activate the seed. The strips 890 may be coupled to the capsule 814 by posts (not shown) to maintain their relative positions during bending.

There have been described and illustrated herein several embodiments of an activatable radioactive therapeutic seed. While particular embodiments of the invention have been described, it is not intended that the invention be limited thereto, as it is intended that the invention be as broad in scope as the art will allow and that the specification be read likewise. For example, those skilled in the art will appreciate that certain features of one embodiment may be combined with features of another embodiment to provide yet additional embodiments. Also, while hot water is disclosed as a heat source for "activating" many of the embodiments of the "activatable" seeds, it will be appreciated that microwave technology or other forms of radiated energy transmitted from a distance or provided at or near the seed implant site may also be used to generate sufficient heat. In addition, while a particular preferred temperature range for melting the radioisotope carrier is disclosed, it will be appreciated that a carrier may be used which melts at any temperature at or between body temperature, i.e., approximately 98° F., and an upper-temperature which will not cause severe damage to body tissue if applied for a very short period of time, i.e., approximately 212° F. Thus, for example, seeds which are intended to be activated at body temperature are preferably stored at room temperature or kept refrigerated prior to use, but may not be handled by the practitioner without substantial activation. Furthermore, it will be appreciated that other types of energy can be used to trigger partial or complete seed "activation". For example, mechanical, electromagnetic, and piezoelectric energy can also be used. In addition, while particular dimensions have been disclosed for the seeds, it will be appreciated that other dimensions may be likewise be used depending on the particular application of the seed; i.e., its locus of implantation. Also, it will be appreciated that the terms "radiotransparent", "radiotranslucent", "radiolucent", and "low Z" are intended to have the same meaning for purpose of the prior description and in the construction of the claims which follow. In addition, the above "activatable" embodiments in conjunction with the "deactivatable" embodiments of the previously incorporated parent case, provide a complete system in which the radiation transmission of a brachytherapy seed can be controllably altered. It will therefore be appreciated by those skilled in the art that yet other modifications could be made to the provided invention without deviating from its spirit and scope as so claimed.

What is claimed is:

1. A radioactive therapeutic seed system, comprising:
a plurality of radioactive therapeutic seeds, wherein
at least one of the therapeutic seeds has means for controllably altering the radiation transmitted through the seed capsule.

2. The system according to claim 1, wherein:
said means for controllably altering the radiation transmitted through the seed capsule includes a radiopaque shield movable between first and second configurations.

3. The system according to claim 1, wherein:
said means for controllably altering the radiation transmitted through the seed capsule includes a shape memory alloy.

4. The system according to claim 1, wherein:
said means for controllably altering the radiation transmitted through the seed capsule includes a spring.

5. The system according to claim 4, wherein:
said means for controllably altering the radiation transmitted through the seed capsule includes a pressurized fluid.

6. The system according to claim 1, wherein:
said means for controllably altering the radiation transmitted through the seed capsule includes a collapsible sleeve.

7. The system according to claim 1, wherein:
said means for controllably altering the radiation transmitted through the seed capsule is responsive to heat.

8. A radioactive therapeutic seed system, comprising:
a plurality of radioactive therapeutic seeds, wherein
at least one of the therapeutic seeds includes means for controllably activating the seed to "turn on" the seed to cause radiation to be emitted therefrom or to increase the radiation emitted therefrom.

9. The system according to claim 8, wherein:
said means for controllably activating includes a movable shield.

10. The system according to claim 8, wherein:
said means for controllably activating is responsive to heat.

11. The system according to claim 8, wherein:
said means for controllably activating includes a spring.

12. The system according to claim 8, wherein:
said means for controllably activating includes radiopaque shape memory metal.

13. The system according to claim 8, wherein:
said means for controllably activating includes metal coated with radiopaque material.

* * * * *